United States Patent
Kawano et al.

(10) Patent No.: US 8,034,755 B2
(45) Date of Patent: Oct. 11, 2011

(54) OIL-IN-WATER TYPE EMULSION COMPOSITION

(75) Inventors: Sayoko Kawano, Yokohama (JP); Yukiko Kamiya, Yokohama (JP); Takeshi Yanagida, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 60 days.

(21) Appl. No.: 12/522,910

(22) PCT Filed: Mar. 21, 2008

(86) PCT No.: PCT/JP2008/000668
§ 371 (c)(1),
(2), (4) Date: Jul. 10, 2009

(87) PCT Pub. No.: WO2008/129806
PCT Pub. Date: Oct. 30, 2008

(65) Prior Publication Data
US 2010/0048442 A1    Feb. 25, 2010

(30) Foreign Application Priority Data

Mar. 29, 2007  (JP) .................................. 2007-087806

(51) Int. Cl.
*A61K 7/50* (2006.01)
(52) U.S. Cl. ...................... 510/130; 510/136; 424/70.14
(58) Field of Classification Search .................. None
See application file for complete search history.

(56) References Cited

U.S. PATENT DOCUMENTS

2010/0247458 A1*  9/2010  Kakoki et al. .................. 424/59

FOREIGN PATENT DOCUMENTS

| JP | 62-221610 A | 9/1987 |
| JP | 2000-178133 A | 6/2000 |
| JP | 2001-233729 A | 8/2001 |
| JP | 2004-168736 A | 6/2004 |
| JP | 2006-290762 A | 10/2006 |

* cited by examiner

*Primary Examiner* — Necholus Ogden, Jr.
(74) *Attorney, Agent, or Firm* — Townsend & Banta

(57) ABSTRACT

The present invention provides an oil-in-water emulsified composition comprising fatty acid soap, the following ingredients (2)-(5) and (6) water.

(2) Polyethylene glycol having an average molecular weight of 2000-25000 in the amount of 0.3-4.0 wt % of the composition,
(3) One, two, or more of nonionic surfactants having a HLB of 10-17 in the amount of 0.1-5.0 wt %,
(4) one, two, or more of nonionic surfactants having a HLB of 2-10 in the amount of 0.1-5.0 wt % of the composition, and
(5) an oil ingredient comprising a solid or semisolid oil ingredient in the amount of 40-70 wt % of the composition.

The object of the present invention is to provide an oil-in-water emulsified composition primarily or secondarily aiming at removing dirt that exhibits no stickiness, superior stability, and richness.

13 Claims, No Drawings

OIL-IN-WATER TYPE EMULSION COMPOSITION

TECHNICAL FIELD

The present invention relates to an oil-in-water emulsified composition; this composition is particularly suitable for use in cleansing creams or massage creams.

BACKGROUND ART

Among oil-in-water emulsified compositions used as external preparation compositions such as cosmetics, there are products that contain fatty acid soaps and aim primarily or secondarily for removing dirt such as cleansing creams and massage creams; the main focus in the development of such products is to maintain the oil-in-water emulsion system from the time of production to just before use, and destroy the emulsion with the hand pressure at the time of use to elute out the oil ingredients in the inner phase to manifest the cleansing effect and massage effect.

In these oil-in-water emulsified compositions, the rich sensation derived from the richness of the composition is an element that improves the value of the product. Conventionally, means such as increasing the ratio of the oil ingredients in the inner phase to the total amount and increasing the ratio of the semisolid oil ingredients are employed to give this richness.

Patent Document 1: JP 2004-168736 A

DISCLOSURE OF INVENTION

Technical Problem

Based on the situation as described above, the object of the present invention is to provide an oil-in-water emulsified composition primarily or secondarily aiming at removing dirt that exhibits no stickiness, superior stability, and richness.

Patent Document 1, which is a prior art technology related to the present invention, discloses a cleansing agent containing 50% or less of water, 1-60% of a polyhydroxy compound, and 1-95% of an oil ingredient; said cleansing agent is a transparent, semi-transparent, or emulsoid cleansing agent in which the oil ingredient is gelated stably without adding a gelling agent. However, the cleansing agent of said prior art document is not an emulsified type so it is difficult to give a rich sensation. Furthermore, said prior art document does not use polyethylene glycol, which is an essential ingredient in the present invention.

Technical Solution

The inventor discovered that the problem described above could be solved by adding polyethylene glycol having a specified range of molecular weight to an oil-in-water emulsified composition primarily or secondarily aiming at removing dirt and maintaining other conditions in specified ranges, and thus completed the present invention.

That is, the present invention provides an oil-in-water emulsified composition comprising (1) fatty acid soap, the following ingredients (2)-(5) and (6) water (hereafter also referred to as "this emulsified composition").
(2) polyethylene glycol having an average molecular weight of 2000-25000 in the amount of 0.3-4.0 wt % of the composition,
(3) one, two, or more of nonionic surfactants having a HLB of 10-17 in the amount of 0.1-5.0 wt % of the composition,
(4) one, two, or more of nonionic surfactants having a HLB of 2-10 in the amount of 0.1-5.0 wt % of the composition, and
(5) an oil ingredient comprising a solid or semisolid oil ingredient in the amount of 40-70 wt % of the composition.

Also, the present invention provides the oil-in-water emulsified composition wherein the solid or semisolid oil ingredient content in said emulsified composition is 5.0-50 wt % of the total amount of the oil ingredients.

Furthermore, the present invention provides the oil-in-water emulsified composition wherein said emulsified composition is a cleansing cream or massage cream.

ADVANTAGEOUS EFFECTS

The present invention provides an oil-in-water emulsified composition primarily or secondarily aiming at removing dirt that exhibits no stickiness, superior stability, and richness.

BEST MODE FOR CARRYING OUT THE INVENTION

Essential Ingredients of the Emulsified Composition (1) Fatty Acid Soap

This emulsified composition can contain one, two or more types of fatty acid soaps regardless of the type as long as they are fatty acid soaps that can be used for external preparations; the fatty acid portion of said fatty acid soap usually has 12-22 carbon atoms, preferably 16-20. In the manufacturing process of this emulsified composition, said fatty acid soap is prepared by separately adding the fatty acid that is to be the fatty acid group of said fatty acid soap and the alkali agent (saponifying agent) to the system so they coexist: said fatty acid is saponified by said alkali agent to generate the fatty acid soap. Examples of said alkali agent include potassium hydroxide, triethanolamine, diethanolamine, basic amino acids, borax, ammonia, taurate, and n-methyltaurate.

Examples of the fatty acid soap that is added to this emulsified composition include sodium laurate, sodium myristate, sodium palmitate, sodium stearate, sodium oleate, potassium laurate, potassium myristate, potassium palmitate, potassium stearate, potassium oleate, monoethanolamine laurate, monoethanolamine myristate, monoethanolamine palmitate, and monoethanolamine stearate.

The blend ratio of the fatty acid soap thus added to this emulsified composition is not limited in particular and can be chosen according to the specific form of this emulsified composition and other ingredients; generally, the fatty acid soap has 12-22 carbon atoms and the blend ratio is 0.3-3.0 wt % of the composition, and preferably the fatty acid soap has 16-20 carbon atoms and the blend ratio is approximately 0.5-2.0 wt % of the composition.

(2) Polyethylene Glycol

This emulsified composition is required to contain polyethylene glycol having an average molecular weight of 2000-25000 (hereafter also referred to as "the specific high molecular weight polyethylene glycol"). If said average molecular weight is less than 2000, then it becomes hard for the composition to give a rich sensation; if it is over 25000, then emulsification becomes difficult and the formulation tends to be unstable.

One, two or more types of the specific high molecular weight polyethylene glycol are added to this emulsified composition; the blend ratio is 0.3-4.0 wt %, preferably 0.5-3.0 wt %, of the composition. If the blend ratio is less than 0.3 wt % of the composition, then it becomes hard for the composition to give a rich sensation; if it is over 4.0 wt %, then there is a strong tendency for the emulsification stability to decrease.

(3) Hydrophilic Nonionic Surfactant

One, two or more types of nonionic surfactants having a HLB of 10-17 are added to this emulsified composition; the blend ratio is 0.1-5.0 wt %, preferably 0.5-3.0 wt %, of the composition. If the blend ratio is outside of this range, the combination balance with the lipophilic nonionic surfactant, described later, becomes poor and there is a stronger tendency for the emulsification stability to decrease.

Selection of said hydrophilic nonionic surfactant is not limited in particular; examples include POE (10-40) glyceryl monostearate, hexaglyceryl monolaurate, decaglyceryl monolaurate, decaglyceryl monomyristate, decaglyceryl monostearate, decaglyceryl monooleate, POE (40-60) castor oil, POE (30-100) hydrogenated castor oil, PEG (40-60) glyceryl triisostearate, PEG (10-60) glyceryl isostearate, PGE (40-60) glyceryl trioleate, PEG (40-60) hydrogenated castor oil isostearate, PEG-60 hydrogenated castor oil triisostearate, PEG (40-60) hydrogenated castor oil laurate, POE (7-20) cetyl ether, and POE (10-50) oleyl ether.

(4) Lipophilic Nonionic Surfactant

One, two or more types of nonionic surfactants having a HLB of 2-10 are added to this emulsified composition; the blend ratio is 0.1-5.0 wt %, preferably 0.5-3.0 wt %, of the composition. If the blend ratio is outside of this range, the combination balance with the aforementioned hydrophilic nonionic surfactant becomes poor and there is a stronger tendency for the emulsification stability to decrease.

Selection of said lipophilic nonionic surfactant is not limited in particular; examples include POE (3) oleyl ether, POE (3) lauryl ether, diglyceryl monostearate, decaglyceryl pentastearate, hexaglyceryl tristearate, POE (2) nonylphenyl ether, glyceryl palmitate, glyceryl isostearate, propylene glycol stearate, PEG (5-7) hydrogenated castor oil, PEG (5-20) glyceryl triisostearate, PEG (3-8) glyceryl isostearate, PEG (3-15) glyceryl tristearate, PEG (5-10) glyceryl trioleate, PEG (10-40) hydrogenated castor oil triisostearate, PEG (5-30) hydrogenated castor oil isostearate, POE sorbitol stearate, POE sorbitol isostearate, and POE sorbitol oleate.

(5) Oil Phase Ingredients (Sometimes Simply Referred to as "the Oil Phase" in this Specification)

This emulsified composition has the oil phase ingredients in the amount of 40-70 wt % of the composition. Here, the oil phase ingredients stand for the totality of the ingredients added as the oil phase when manufacturing the oil-in-water emulsified composition; specifically they are mainly oil ingredients (liquid oil ingredients, semisolid oil ingredients, and solid oil ingredients), surfactants (liquid surfactants, semisolid surfactants, and solid surfactants), and fatty acids. In addition to the ingredients mentioned above, oil soluble preservatives, ultraviolet absorbents, oil soluble drugs, antioxidants, and perfumes may be added. If the oil phase is less than 40 wt % of the composition, then the stability is satisfactory, but the makeup does not come off well and the composition tends to resist spreading; if it is more than 70 wt %, then the stability is poor and stickiness is felt during use.

For this emulsified composition, the aforementioned oil phase ingredients are required to contain solid or semisolid oil ingredients.

A "solid or semisolid oil ingredient" refers to an oil ingredient whose melting point is room temperature (about 20-25° C.) or higher; specific examples include waxes such as candelilla wax, beeswax, cotton wax, carnauba wax, bayberry wax, tree wax, montan wax, bran wax, lanolin, reduced lanolin, hard lanolin, kapok wax, sugar cane wax, jojoba wax, and shellac wax; higher alcohols that are solid at room temperature such as cetyl alcohol and stearyl alcohol; and solid oil ingredients such as cacao oil, hydrogenated castor oil, Japanese core oil, and shea butter.

The blend ratio of the solid or semisolid oil ingredients in the oil phase of this emulsified composition is 5.0-50 wt %, preferably 10-35 wt %, of the total amount of the oil phase. If the ratio of the solid or semisolid oil ingredients is less than 5.0 wt % of the total amount of the oil phase, then the richness of the cream tends to decrease; if it is over 50 wt %, then the stability decreases and stickiness is felt during use.

As described above, in addition to the aforementioned solid or semisolid oil ingredients, it is possible to add a liquid oil ingredient that is liquid at room temperature (as described above) as a constituent ingredient of the oil phase. Selection of the liquid oil ingredient is not limited in particular; examples include liquid oils and fats such as linseed oil, tsubaki oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cotton seed oil, soybean oil, peanut oil, tea seed oil, evening primrose oil, egg yolk oil, liver oil, triglycerin, glyceryl trioctanoate, and glyceryl triisopalmitate; octanoic esters such as cetyl octanoate; isooctanoic esters such as glyceryl tri-2-ethylhexaenoate and pentaerythritol tetra-2-ethylhexanoate; lauric esters such as hexyl laurate; myristic esters such as isopropyl myristate and octyldodecyl myristate; palmitic esters such as octyl palmitate; isostearic esters such as isocetyl stearate; isostearic esters such as isopropyl isostearate; isopalmitic esters such as octyl isopalmitate; oleic esters such as isodecyl oleate; adipic diesters such as diisopropyl adipate; sebacic diesters such as diethyl sabacate; and ester oils such as diisostearyl malate; and liquid hydrocarbon oils such as liquid paraffin and squalane.

Furthermore, for the silicone oil, it is possible to use chain silicones such as dimethylpolysiloxane, methylphenylpolysiloxane, and methyhydrogenpolysiloxane; cyclic silicones such as octamethylcyclotetrasiloxane, decamethylcyclopentasiloxane, and dodecamethylcyclohexasiloxane; silicone resins capable of forming a three dimensional network structure such as amino-modified silicone oil, polyether-modified silicone oil, carboxy-modified silicone oil, alkyl-modified silicone oil, ammonium salt-modified silicone oil, fluorine-modified silicone oil, and trimethylsiloxysilicic acid; high polymer methylpolysiloxane such as high polymer dimethylpolysiloxane, high polymer methylphenylpolysiloxane, and high polymer methylvinylpolysiloxane; and high polymer amino-modified methylpolysiloxane. Also, for the silicone surfactant, it is possible to add dimethicone polyol and such.

(6) Water

This emulsified composition is an oil-in-water type emulsified composition and it is essential for it to contain water. The blend ratio is the balance of the ingredients other than water; it is generally in the range of 10-50 wt %.

"General Ingredients of this Emulsified Composition"

In addition to the aforementioned essential ingredients, general ingredients used in external preparations such as cosmetics can be added to this emulsified composition within the qualitative or quantitative range that does not affect the effect of the present invention. Examples of said general ingredients include surfactants other than those described above, powders, antibacterial agents, drugs, tonics, thickeners, ultraviolet absorbents, antioxidants, preservatives, perfumes, and pigments.

"Preparation of this Emulsified Composition"

This emulsified composition can be prepared with a conventional preparation method for emulsified compositions; specifically, the emulsifier-in-water method, the emulsifier-in-oil method, and the alternate addition method.

As mentioned above, this emulsified composition is an oil-in-water emulsified composition; as long as it is so it can be cream or emulsion, but it is suitable for use in products primarily or secondarily aiming at removing dirt. The most preferable applications for the present invention are cleansing creams for removing cosmetics and facial massage creams. The composition can become a cushion between the hand and skin during cosmetic removal and massage to alleviate the skin strain due to stimulation such as friction.

The main optional ingredients in this emulsified composition that can be in these forms, in addition to the aforementioned essential ingredients, include, as the water phase ingredients for example, one, two, or more humectants such as glycerin, propylene glycol, dipropylene glycol, 1,3-butylene glycol, low molecular weight polyethylene glycol, sorbitol, maltitol, pyrrolidonecarboxylic soda, hyaluronic acid, and chondroitin sulfate in the amount of 5.0-50 wt %, preferably 10-35 wt %, of the total amount of the water phase; thickeners such as bentonite, carboxyvinyl polymer, hydroxypropyl cellulose, POP, and POE thickeners in the amount of 0.2-2.0 wt %, preferably 0.5-1.5 wt %, of the total amount of the water phase; water soluble preservatives such as methylparaben, hibitane glycolate, and phenoxyethanol; as well as water soluble drugs, crude drugs, germicides, sequestering agents, dyes, and pigment powders; these can be added to this emulsified composition as necessary.

EXAMPLES

The present invention is described below by referring to Examples, but this is not to limit the scope of the present invention. The blend ratios are in wt % units.

Test Examples

1. Formulations of Test Samples

In order to verify the effect of the present invention, formulations of the oil-in-water creams shown in Table 1 were prepared and "stability", "richness at initial spread", and "stickiness after being wiped off" were evaluated based on the criteria described in the following 2. The results are also described in Table 1.

The oil-in-water cream of each sample shown in Table 1 was prepared by thoroughly dissolving the oil phase (oil ingredients, fatty acids, nonionic surfactants, and perfumes) and the water phase (other than the oil phase) separately at 70° C., adding the oil phase to the water phase, emulsifying the mixture by using an emulsifier, and then cooling the emulsion with a heat exchanger down to 35° C. and putting it in a container.

2. Evaluation Criteria (1) Stability

Each test sample was left alone for one month at 0° C., 50° C., and room temperature, and the external appearance, state, color, odor, etc. of the sample was investigated; comprehensive evaluation was made based on the following criteria.

0: No change from the initial state.

Δ: Some coalescing of the emulsified particles is observed but there seems to be no problem in terms of stability.

X: Stability is very poor and separation is observed particularly at 50° C.

(2) Richness at the Time of Application/Massage 2.5 g was put on a hand and spread on the face, and sensory evaluation was conducted; evaluation was done by comparison with the basic formulation (in Table 1, the evaluation column for the basic formulation is entered as "–".)

0: Richness is felt abundantly.

0Δ: More richness is felt compared with the basic formulation.

Δ: Richness equivalent of that of the basic formulation is felt.

X: Richness is not felt and the initial spread is light.

(3) Stickiness after being Wiped Off

After letting an appropriate amount be absorbed on the face, the sample was wiped off with tissue paper and the residual sensation was evaluated.

0: No stickiness remains and adequately moist tactile sensation remains.

Δ: Some stickiness remains.

X: Stickiness remains to the point where one wants to rub with tissue paper several times.

TABLE 1

| | Blend ratio (wt %) | | | | | | | | | |
| --- | --- | --- | --- | --- | --- | --- | --- | --- | --- | --- |
| | Basic formulation | Example 1 | Example 2 | Example 3 | Example 4 | Comparative example 1 | Comparative example 2 | Comparative example 3 | Comparative example 4 | Comparative example 5 |
| <Ingredients> (Oil ingredients) | | | | | | | | | | |
| Petrolatum | 7.0 | 7.0 | 7.0 | 7.0 | 7.0 | 9.0 | 8.0 | 7.0 | 7.0 | 7.0 |
| Hydrogenated palm oil | — | — | — | — | — | — | 1.0 | — | — | — |
| Stearyl alcohol | 1.1 | 1.1 | 1.1 | 1.1 | 1.1 | 1.1 | 1.1 | 1.1 | 1.1 | 1.1 |
| Batyl alcohol | 1.1 | 1.1 | 1.1 | 1.1 | 1.1 | 1.1 | 1.1 | 1.1 | 1.1 | 1.1 |
| Cetyl ethylhexanoate | 9.0 | 9.0 | 9.0 | 9.0 | 9.0 | 9.0 | 9.0 | 9.0 | 9.0 | 9.0 |
| Mineral oil | 41.0 | 41.0 | 41.0 | 41.0 | 41.0 | 41.0 | 41.0 | 41.0 | 41.0 | 41.0 |
| Squalane | 0.5 | 0.5 | 0.5 | 0.5 | 0.5 | 0.5 | 0.5 | 0.5 | 0.5 | 0.5 |
| (Surfactant) | | | | | | | | | | |
| Stearic acid | 1.5 | 1.5 | 1.5 | 1.5 | 1.5 | 1.5 | 1.5 | 1.5 | 1.5 | 1.5 |
| PEG-hydrogenated castor oil | 1.5 | 1.5 | 1.5 | 1.5 | 1.5 | 1.5 | 1.5 | 1.5 | 1.5 | 1.5 |
| PEG-5 glyceryl stearate | 1.0 | 1.0 | 1.0 | 1.0 | 1.0 | 1.0 | 1.0 | 1.0 | 1.0 | 1.0 |

TABLE 1-continued

| | Basic formulation | Example 1 | Example 2 | Example 3 | Example 4 | Comparative example 1 | Comparative example 2 | Comparative example 3 | Comparative example 4 | Comparative example 5 |
|---|---|---|---|---|---|---|---|---|---|---|
| | | | | Blend ratio (wt %) | | | | | | |
| Sodium cocoylmethyltaurate | 0.1 | 0.1 | 0.1 | 0.1 | 0.1 | 0.1 | 0.1 | 0.1 | 0.1 | 0.1 |
| Dimeticone copolyol (Humectant) | 2.0 | 2.0 | 2.0 | 2.0 | 2.0 | 2.0 | 2.0 | 2.0 | 2.0 | 2.0 |
| Polyethylene glycol 1000 | — | — | — | — | — | — | — | 5.0 | 3.0 | — |
| Polyethylene glycol 4000 | — | 3.0 | — | — | — | — | — | — | — | — |
| Polyethylene glycol 6000 | — | — | 2.5 | — | — | — | — | — | — | — |
| Polyethylene glycol 11000 | — | — | — | 1.5 | — | — | — | — | — | — |
| Polyethylene glycol 20000 | — | — | — | — | 1.0 | — | — | — | — | — |
| Glycerin | 2.5 | 2.5 | 2.5 | 2.5 | 2.5 | 2.5 | 2.5 | 2.5 | 2.5 | 2.5 |
| 1,3-butylene glycol (Saponifying agent) | 5.5 | 5.5 | 5.5 | 5.5 | 5.5 | 5.5 | 5.5 | 5.5 | 5.5 | 5.5 |
| Potassium hydroxide (Others) | 0.1 | 0.1 | 0.1 | 0.1 | 0.1 | 0.1 | 0.1 | 0.1 | 0.1 | 0.1 |
| Chelating agent | *AA | *AA | *AA | *AA | *AA | *AA | *AA | *AA | *AA | *AA |
| Preservative | *AA | *AA | *AA | *AA | *AA | *AA | *AA | *AA | *AA | *AA |
| Xanthan gum | 0.01 | 0.01 | 0.01 | 0.01 | 0.01 | 0.01 | 0.01 | 0.01 | 0.01 | 0.01 |
| Perfume | *AA | *AA | *AA | *AA | *AA | *AA | *AA | *AA | *AA | *AA |
| Ion-exchanged water | Balance | Balance | Balance | Balance | Balance | Balance | Balance | Balance | Balance | Balance |
| <Results> | | | | | | | | | | |
| Stability | ○ | ○ | ○ | ○ | ○ | Δ | ○ | Δ | ○ | X |
| Richness at the time of application/massage | — | ○ | ○ | ○ | ○ | ○ | Δ | ○Δ | Δ | — |
| Stickiness after being wiped off | ○ | ○ | ○ | ○ | ○ | X | Δ | ○ | ○ | — |

*AA: Appropriate amount

Stearic acid exists as sodium stearate due to saponification.
Polyethylene glycol 1000: Average molecular weight 950-1050
Polyethylene glycol 4000: Average molecular weight 3000-3700
Polyethylene glycol 6000: Average molecular weight 6000-7500
Polyethylene glycol 11000: Average molecular weight 9300-12500
Polyethylene glycol 20000: Average molecular weight 15500-25000
These results indicate that the increase in the relative amount of the oil phase or in the solid or semisolid oil ingredients in the formulation, as attempted in Comparative examples 1 and 2, would result in problems such as stickiness after being wiped off and decreased stability. When polyethylene glycol 1000 (average molecular weight 950-1050), which is low molecular weight and liquid at room temperature, is used, richness was not felt if the blend ratio was 3.0% or less and the stability worsened if the blend ratio was 5.0% or more (Comparative examples 3 and 4). When polyethylene glycol 4000 (average molecular weight 3000-3700), which is high molecular weight and solid at room temperature, was used, sufficient richness was felt if the blend ratio was 3.0% (Example 1). When it was over 4.0%, the emulsification became unstable Comparative Example 5

Similarly, polyethylene glycol 6000 (average molecular weight 6000-7500), 11000 (average molecular weight 9300-12500), and 20000 (average molecular weight 15500-25000) were used for evaluation and the aforementioned results were obtained (Examples 2-4).

Formulation examples of the present invention are disclosed below. In the following formulation examples, the fatty acids and alkali agents are saponified and thus exist in the final products as fatty acid soaps.

| "Formulation example 1" Cleansing cream | |
|---|---|
| Ingredients | Blend ratio (wt %) |
| (A) | |
| Mineral oil | 41.0 |
| Olefin oligomer | 9.0 |
| Petrolatum | 4.0 |
| Microcrystalline wax | 1.0 |
| Behenic acid | 1.0 |
| Stearyl alcohol | 2.0 |
| Squalane | 0.5 |
| PEG (30) stearate | 1.2 |
| POE (10) hydrogenated castor oil | 0.9 |
| Monoglyceride stearate | 0.5 |
| Perfume | Appropriate amount |
| (B) | |
| 1,3-butylene glycol | 5.5 |
| Potassium hydroxide | 0.1 |
| Preservative | Appropriate amount |
| Xanthan gum | 0.04 |
| Polyethylene glycol 4000 | 3.0 |
| Chelating agent | Appropriate amount |
| Ion-exchanged water | Balance |

<Preparation Method>

Oil phase A and water phase B are thoroughly dissolved at 70° C. and A is added to B, followed by emulsification with an emulsifier. The emulsified product is cooled down to the final temperature of 35° C. by using a heat exchanger and then put into a container.

"Formulation example 2" Cleansing cream

| Ingredients | Blend ratio (wt %) |
|---|---|
| (A) | |
| Olefin oligomer | 35.0 |
| Beeswax | 3.0 |
| Petrolatum | 10.0 |
| Triethylhexanoin | 2.0 |
| Stearic acid | 1.0 |
| Stearyl alcohol | 2.0 |
| Squalane | 5.0 |
| PEG (40) hydrogenated castor oil isostearate | 1.8 |
| Glyceryl monostearate | 0.2 |
| PEG (5) glyceryl stearate | 0.7 |
| Perfume | Appropriate amount |
| (B) | |
| Propylene glycol | 2.0 |
| Glycerin | 3.0 |
| Potassium hydroxide | 0.1 |
| Preservative | Appropriate amount |
| Xanthan gum | 0.01 |
| Polyethylene glycol 6000 | 2.5 |
| Chelating agent | Appropriate amount |
| Ion-exchanged water | Balance |

<Preparation Method>

Based on Formulation example 1.

"Formulation example 3" Cleansing cream

| Ingredients | Blend ratio (wt %) |
|---|---|
| (A) | |
| Mineral oil | 40.5 |
| Cetyl ethylhexanoate | 9.0 |
| Petrolatum | 7.0 |
| Dimethicone polyol | 2.0 |
| Stearic acid | 1.3 |
| Stearyl alcohol | 1.0 |
| Batyl alcohol | 1.0 |
| Squalane | 0.5 |
| POE (30) hydrogenated castor oil | 1.5 |
| PEG (5) glyceryl stearate | 1.1 |
| Perfume | Appropriate amount |
| (B) | |
| 1,3-butylene glycol | 5.0 |
| Glycerin | 3.0 |
| Sodium hydroxide | 0.1 |
| Preservative | Appropriate amount |
| Carbomer | 0.04 |
| Polyethylene glycol 11000 | 1.5 |
| Chelating agent | Appropriate amount |
| Ion-exchanged water | Balance |

<Preparation Method>

Based on Formulation example 1.

"Formulation example 4" Cleansing cream

| Ingredients | Blend ratio (wt %) |
|---|---|
| (A) | |
| Mineral oil | 20.0 |
| Cetyl ethylhexanoate | 9.0 |
| Petrolatum | 5.0 |
| Triethylhexanoin | 2.0 |
| Stearic acid | 1.0 |
| Stearyl alcohol | 1.0 |
| Behenyl alcohol | 1.0 |
| Squalane | 20.0 |
| POE(60) hydrogenated castor oil | 1.2 |
| Sorbitan stearate | 1.2 |
| Perfume | Appropriate amount |
| (B) | |
| Dipropylene glycol | 5.0 |
| Potassium hydroxide | 0.1 |
| Preservative | Appropriate amount |
| Carbomer | 0.04 |
| Polyethylene glycol 20000 | 1.0 |
| Chelating agent | |
| Ion-exchanged water | Balance |

<Preparation Method>

Based on Formulation example 1.

"Formulation example 5" Massage cream

| Ingredients | Blend ratio (wt %) |
|---|---|
| (A) | |
| Squalane | 25.0 |
| Pentaerythritol tetra-2-ethylhexanoate | 5.0 |
| Hydrogenated palm oil | 5.0 |
| Microcrystalline wax | 3.0 |
| Stearyl alcohol | 1.5 |
| Behenyl alcohol | 0.5 |
| Stearic acid | 2.0 |
| Monoglyceride stearate | 1.3 |
| PEG (5) glyceryl stearate | 2.8 |
| POE(20) sorbitan monostearate | 0.5 |
| Perfume | Appropriate amount |
| (B) | |
| Glycerin | 4.0 |
| Isopropylene glycol | 2.0 |
| Polyethylene glycol 400 | 3.0 |
| Polyethylene glycol 20000 | 1.1 |
| Sodium hydroxide | 0.03 |
| Potassium hydroxide | 0.07 |
| Carbomer | 0.03 |
| Chelating agent | Appropriate amount |
| Preservative | Appropriate amount |
| Ion-exchanged water | Balance |

\<Preparation Method\>
Based on Formulation example 1.

"Formulation example 6" Massage cream

| Ingredients | Blend ratio (wt %) |
|---|---|
| (A) | |
| Mineral oil | 28.0 |
| Petrolatum | 5.0 |
| Solid paraffin | 4.0 |
| Cetyl alcohol | 1.5 |
| Stearyl alcohol | 1.5 |
| Stearic acid | 0.8 |
| Palmitic acid | 1.2 |
| Self-emulsified monoglyceride stearate | 2.0 |
| POE(40) hydrogenated castor oil | 2.5 |
| Perfume | Appropriate amount |
| (B) | |
| Propylene glycol | 5.0 |
| Sorbit solution | 5.0 |
| Triethanolamine | 2.2 |
| Carbomer | 0.04 |
| Xanthan gum | 0.01 |
| Polyethylene glycol 6000 | 1.7 |
| Preservative | Appropriate amount |
| Chelating agent | Appropriate amount |
| Ion-exchanged water | Balance |

\<Preparation Method\>
Based on Formulation example 1.

INDUSTRIAL APPLICABILITY

The oil-in-water emulsified composition of the present invention can be used for external preparations. It is particularly suitable to be used for cleansing creams or massage creams.

The invention claimed is:

1. An oil-in-water emulsified composition comprising:
(1) fatty acid soap,
(2) Polyethylene glycol having an average molecular weight of 2000-25000 in the amount of 0.3-4.0 wt % of the composition,
(3) one or more nonionic surfactants having a HLB of 10-17 in the amount of 0.1-5.0 wt % of the composition,
(4) one or more nonionic surfactants having a HLB of 2-10 in the amount of 0.1-5.0 wt % of the composition,
(5) an oil ingredient comprising a solid or semisolid oil ingredient in the amount of 40-70 wt % of the composition; and
(6) water.

2. The oil-in-water emulsified composition of claim 1, wherein the solid or semisolid oil ingredient content in said emulsified composition is 5.0-50 wt % of the total amount of the oil ingredient.

3. The oil-in-water emulsified composition of claim 1, wherein said emulsified composition is a cleansing cream or massage cream.

4. The oil-in-water emulsified composition of claim 2, wherein said emulsified composition is a cleansing cream or massage cream.

5. The oil-in-water emulsified composition of claim 1, wherein the fatty acid soap comprises a fatty acid portion having 12-22 carbon atoms.

6. The oil-in-water emulsified composition of claim 1, wherein the fatty acid soap is one or more of sodium laurate, sodium myristate, sodium palmitate, sodium stearate, sodium oleate, potassium laurate, potassium myristate, potassium palmitate, potassium stearate, potassium oleate, monoethanolamine laurate, monoethanolamine myristate, monoethanolamine palmitate, and monoethanolamine stearate.

7. The oil-in-water emulsified composition of claim 1, wherein the fatty acid soap is present in a blend ratio is 0.3-3.0 wt % of the composition.

8. The oil-in-water emulsified composition of claim 1, wherein the one or more nonionic surfactants having an HLB of 10-17 are one or more hydrophilic nonionic surfactants selected from the group consisting of POE (10-40) glyceryl monostearate, hexaglyceryl monolaurate, decaglyceryl monolaurate, decaglyceryl monomyristate, decaglyceryl monostearate, decaglyceryl monooleate, POE (40-60) castor oil, POE (30-100) hydrogenated castor oil, PEG (40-60) glyceryl triisostearate, PEG (10-60) glyceryl isostearate, PGE (40-60) glyceryl trioleate, PEG (40-60) hydrogenated castor oil isostearate, PEG-60 hydrogenated castor oil triisostearate, PEG (40-60) hydrogenated castor oil laurate, POE (7-20) cetyl ether, and POE (10-50) oleyl ether.

9. The oil-in-water emulsified composition of claim 1, wherein the one or more nonionic surfactants having an HLB of 2-10 are one or more lipophilic nonionic surfactants selected from the group consisting of POE (3) oleyl ether, POE (3) lauryl ether, diglyceryl monostearate, decaglyceryl pentastearate, hexaglyceryl tristearate, POE (2) nonylphenyl ether, glyceryl palmitate, glyceryl isostearate, propylene glycol stearate, PEG (5-7) hydrogenated castor oil, PEG (5-20) glyceryl triisostearate, PEG (3-8) glyceryl isostearate, PEG (3-15) glyceryl tristearate, PEG (5-10) glyceryl trioleate, PEG (10-40) hydrogenated castor oil triisostearate, PEG (5-30) hydrogenated castor oil isostearate, POE sorbitol stearate, POE sorbitol isostearate, and POE sorbitol oleate.

10. The oil-in-water emulsified composition of claim 1, wherein the solid or semisolid oil ingredient is one or more of candelilla wax, beeswax, cotton wax, carnauba wax, bayberry wax, tree wax, montan wax, bran wax, lanolin, reduced lanolin, hard lanolin, kapok wax, sugar cane wax, jojoba wax, shellac wax, cetyl alcohol, stearyl alcohol, cacao oil, hydrogenated castor oil, Japanese core oil, and shea butter.

11. The oil-in-water emulsified composition of claim 1, wherein the oil ingredient comprises one or more liquid oil components selected from the group consisting of linseed oil, tsubaki oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cotton seed oil, soybean oil, peanut oil, tea seed oil, evening primrose oil, egg yolk oil, liver oil, triglycerin, glyceryl trioctanoate, glyceryl triisopalmitate, cetyl octanoate, glyceryl tri-2-ethylhexaenoate, pentaerythritol tetra-2-ethylhexanoate, hexyl laurate, isopropyl myristate, octyldodecyl myristate, octyl palmitate, isocetyl stearate, isopropyl isostearate, octyl isopalmitate, isodecyl oleate, diisopropyl adipate, diethyl sabacate, diisostearyl malate, liquid paraffin and squalane.

12. The oil-in-water emulsified composition of claim 1, wherein the oil ingredient comprises one or more of chain silicones selected from the group consisting of dimethylpolysiloxane, methylphenylpolysiloxane, and methyhydrogenpolysiloxane; cyclic silicones selected from the group consisting of octamethylcyclotetrasiloxane, decamethylcyclopentasiloxane, and dodecamethylcyclohexasiloxane; silicone resins capable of forming a three dimensional network structure selected from the group consisting of amino-modified silicone oil, polyether-modified silicone oil, carboxy-modified silicone oil, alkyl-modified silicone oil, ammonium salt-modified silicone oil, fluorine-modified silicone oil, and trimethylsiloxysilicic acid; high polymer methylpolysiloxane selected from the group consisting of high polymer dimethylpolysiloxane, high polymer methylphenylpolysiloxane, and high polymer methylvinylpolysiloxane; and high polymer amino-modified methylpolysiloxane.

13. A method of cleansing skin via application of an oil-in-water emulsion thereto comprising:
(A) applying to the skin an oil-in-water emulsified composition comprising:
  (1) fatty acid soap,
  (2) 0.3-4.0 wt % polyethylene glycol having an average molecular weight of 2000-25000,
  (3) 0.1-5.0 wt % of one or more of nonionic surfactants having a HLB of 10-17,
  (4) 0.1-5.0 wt % of one or more of nonionic surfactants having a HLB of 2-10,
  (5) 40-70 wt % of an oil ingredient comprising a solid or semisolid oil ingredient; and
  (6) water; and
(B) massaging said oil-in-water emulsified composition into the skin so as to apply sufficient pressure to destroy the emulsion, thereby eluting out the oil ingredients in the inner phase.

* * * * *